United States Patent
Biancalana et al.

(10) Patent No.: US 10,729,582 B2
(45) Date of Patent: Aug. 4, 2020

(54) VITRECTOMY PROBE WITH END TISSUE CUTTER AND ASSOCIATED DEVICES, SYSTEMS, AND METHODS

(71) Applicant: Novartis AG, Basel (CH)

(72) Inventors: Philip John Biancalana, Keller, TX (US); Paul R. Hallen, Colleyville, TX (US); Mark Alan Hopkins, Mission Viejo, CA (US); Michael J. Papac, North Tustin, CA (US); Robert Joseph Sanchez, Jr., Oceanside, CA (US); Salomon Valencia, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 72 days.

(21) Appl. No.: 15/591,727

(22) Filed: May 10, 2017

(65) Prior Publication Data
US 2017/0333252 A1    Nov. 23, 2017

Related U.S. Application Data

(60) Provisional application No. 62/337,596, filed on May 17, 2016.

(51) Int. Cl.
*A61F 9/007*    (2006.01)
*A61B 17/3209*    (2006.01)

(52) U.S. Cl.
CPC ...... *A61F 9/00763* (2013.01); *A61F 9/00736* (2013.01); *A61B 2217/005* (2013.01)

(58) Field of Classification Search
CPC .............. A61F 9/00763; A61F 9/00736; A61F 9/00745–00754; A61F 9/013–0133; A61F 9/008; A61B 17/3207; A61B 17/320758–2017/320775; A61B 17/320016–2017/320032
See application file for complete search history.

(56) References Cited

U.S. PATENT DOCUMENTS

| | | | |
|---|---|---|---|
| 4,246,902 A * | 1/1981 | Martinez | A61F 9/00763 604/22 |
| 4,320,761 A | 3/1982 | Haddad | |
| 4,517,977 A * | 5/1985 | Frost | A61B 17/32002 604/22 |
| 4,877,026 A | 10/1989 | de Laforcade | |
| 5,176,628 A | 1/1993 | Charles et al. | |
| 5,263,958 A | 11/1993 | deGuillebon et al. | |
| 5,275,609 A | 1/1994 | Pingleton et al. | |

(Continued)

*Primary Examiner* — Katrina M Stransky
*Assistant Examiner* — Brigid K Byrd

(57) ABSTRACT

Systems, apparatuses, and methods of and for an ophthalmic surgical system are disclosed. An ophthalmic surgical system may include a vitreous probe having a housing sized and shaped for grasping by a user. The vitreous probe may also include a cutter extending from the housing and being sized to penetrate and treat a patient eye. The cutter may include an outer cutting tube coupled to the housing. The outer cutting tube may have an outer port formed at a distal end wall of the outer cutting tube and configured to receive tissue. The cutter may include a rotatable inner cutting member disposed within the outer cutting tube. The inner cutting member may include a first cutting surface that rotates across the outer port to cut the tissue when the inner cutting member is rotated.

18 Claims, 10 Drawing Sheets

(56) References Cited

U.S. PATENT DOCUMENTS

| | | |
|---|---|---|
| 5,383,884 A | 1/1995 | Summers |
| 5,562,693 A | 10/1996 | Devlin et al. |
| 5,807,401 A | 9/1998 | Grieshaber et al. |
| 6,007,513 A | 12/1999 | Anis et al. |
| 6,908,476 B2 | 6/2005 | Jud et al. |
| 9,615,969 B2 | 4/2017 | Nissan et al. |
| 2007/0185512 A1 | 8/2007 | Kirchhevel |
| 2008/0208233 A1 | 8/2008 | Barnes et al. |
| 2008/0281254 A1* | 11/2008 | Humayun ............... A61B 90/98 604/22 |
| 2011/0196400 A1* | 8/2011 | Robertson ........ A61B 17/22004 606/169 |
| 2012/0022434 A1* | 1/2012 | Lue ..................... A61F 9/00763 604/22 |
| 2012/0041358 A1* | 2/2012 | Mann .................. A61F 9/00763 604/22 |
| 2013/0144317 A1* | 6/2013 | Valencia ............. A61F 9/00763 606/170 |
| 2014/0074013 A1 | 3/2014 | McCary et al. |
| 2014/0171997 A1* | 6/2014 | Nissan ................ A61F 9/00763 606/171 |
| 2016/0067091 A1 | 3/2016 | Wells et al. |
| 2018/0008463 A1 | 1/2018 | Charles |
| 2018/0271705 A1 | 9/2018 | Valencia |

* cited by examiner

VITRECTOMY PROBE WITH END TISSUE CUTTER AND ASSOCIATED DEVICES, SYSTEMS, AND METHODS

PRIORITY CLAIM

This application claims the benefit of priority of U.S. Provisional Patent Application Ser. No. 62/337,596 titled "Vitrectomy Probe with End Tissue Cutter and Associated Devices, Systems and Methods", filed on May 17, 2016, whose inventors are Philip John Biancalana, Paul R. Hallen, Mark Alan Hopkins, Michael J. Papac, Robert Joseph Sanchez, Jr., and Salomon Valencia, which is hereby incorporated by reference in its entirety as though fully and completely set forth herein.

TECHNICAL FIELD

The present disclosure is directed to ophthalmic surgical devices, systems, and methods. More particularly, but not by way of limitation, the present disclosure is directed to a vitreous probe with an end tissue cutter and associated devices, systems, and methods.

BACKGROUND

Microsurgical procedures frequently require precision cutting and/or removing of various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g., cutting and removal of vitreous near a detached portion of the retina or a retinal tear), vitreous base dissection, and cutting and removal of membranes are particularly difficult.

Conventional vitrectomy probes typically include a hollow outer cutting member, a hollow inner cutting member arranged coaxially with and movably disposed within the hollow outer cutting member, and a port formed on a side wall of the outer cutting member. Vitreous humor and/or membranes are aspirated into the open port, and the inner member is actuated, closing the port. As the port closes, cutting surfaces on both the inner and outer cutting members cooperate to cut the vitreous and/or membranes. The cut tissue is then aspirated away through the inner cutting member. Because the port is formed on the side wall of the outer cutting member, the conventional vitrectomy probe may require the surgeon to maneuver the conventional vitrectomy probe in order to engage a tissue. Further, the port to tip distance (PTTD) of a conventional vitrectomy probe is typically about 0.009"-0.015". The PTTD should be reduced (e.g., ideally at 0") to improve surgical precision.

SUMMARY

The present disclosure describes an example vitreous probe. The vitreous probe may include a housing and a cutter extending from the housing and configured to penetrate and treat an eye of a patient. The cutter may include an outer cutting tube coupled to the housing and an inner cutting member. The outer cutting tube may have an outer port formed at a distal end wall of the outer cutting tube and configured to receive tissue. The inner cutting member may be disposed within the outer cutting tube to cut tissue received in the outer port.

The inner cutting member may include a cutting blade configured to move across the outer port and coordinate with the outer port to cut tissue received in the outer port. The inner cutting member may include a rod extending in the outer cutting tube along a longitudinal direction of the outer cutting tube and the cutting blade is disposed at a distal end of the rod. In some embodiments, the outer cutting tube may include a lumen sized to pass tissue adjacent the rod for aspiration from the eye. In other embodiments, the rod may include an aspiration lumen configured to aspirate tissue from the eye. The cutting blade may include a cutting edge and the rod is driven by a motor or an actuator to rotate the cutting blade with the cutting edge being a leading edge.

In some embodiments, the inner cutting member may include two or more cutting blades and the outer cutting tube may include two or more outer ports. The two or more cutting blades and the two or more outer ports are configured to coordinate with each other to perform two or more cutting operations simultaneously. In some embodiments, the inner cutting member may include a laser cutting device configured to ablate tissue received in the outer port.

Further, the present disclosure describes an example ophthalmic surgical system. The system may include a vitrectomy probe and a controller. The vitrectomy probe may include a housing and a cutter extending from the housing and configured to penetrate and treat an eye of a patient. The cutter may include an outer cutting tube with an outer port formed at a distal end wall of the outer cutting tube and configured to receive tissue. The cutter also may include an inner cutting member disposed within the outer cutting tube to cut tissue received in the outer port and an actuator configured to impart rotational motion to the inner cutting member. The ophthalmic surgical system may include a controller configured to drive the actuator to rotate the inner cutting member. In some embodiments, the actuator is configured to rotate the inner cutting member continuously in a particular direction. In other embodiments, the actuator is configured to reciprocate the inner cutting member to move back and forth between two opposite directions. In an embodiment, the vitrectomy probe may include a Radio Frequency Identification (RFID) tag indicating a type of vitrectomy probe and the controller is configured to detect the type of vitrectomy probe based on the RFID tag and set an actuation speed and an actuation range of the inner cutting member based on the type of vitrectomy probe.

In addition, the present disclosure is directed to ophthalmic surgical methods. An exemplary method may include inserting a cutter of a vitreous probe into a vitreous chamber of an eye of a patient. The cutter may include an outer cutting tube having an outer port formed at a distal end wall of the outer cutting tube and configured to receive tissue. The cutter also may include a rotatable inner cutting member positioned within the outer cutting tube and rotatable past the outer port. The method may include rotating the inner cutting member to cut tissue in the outer port. In some embodiments, the method may include rotating the inner cutting member in alternating first and second directions. The method also may include adjusting one or more of an actuation speed and an actuation range of the inner cutting member based on a control signal.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
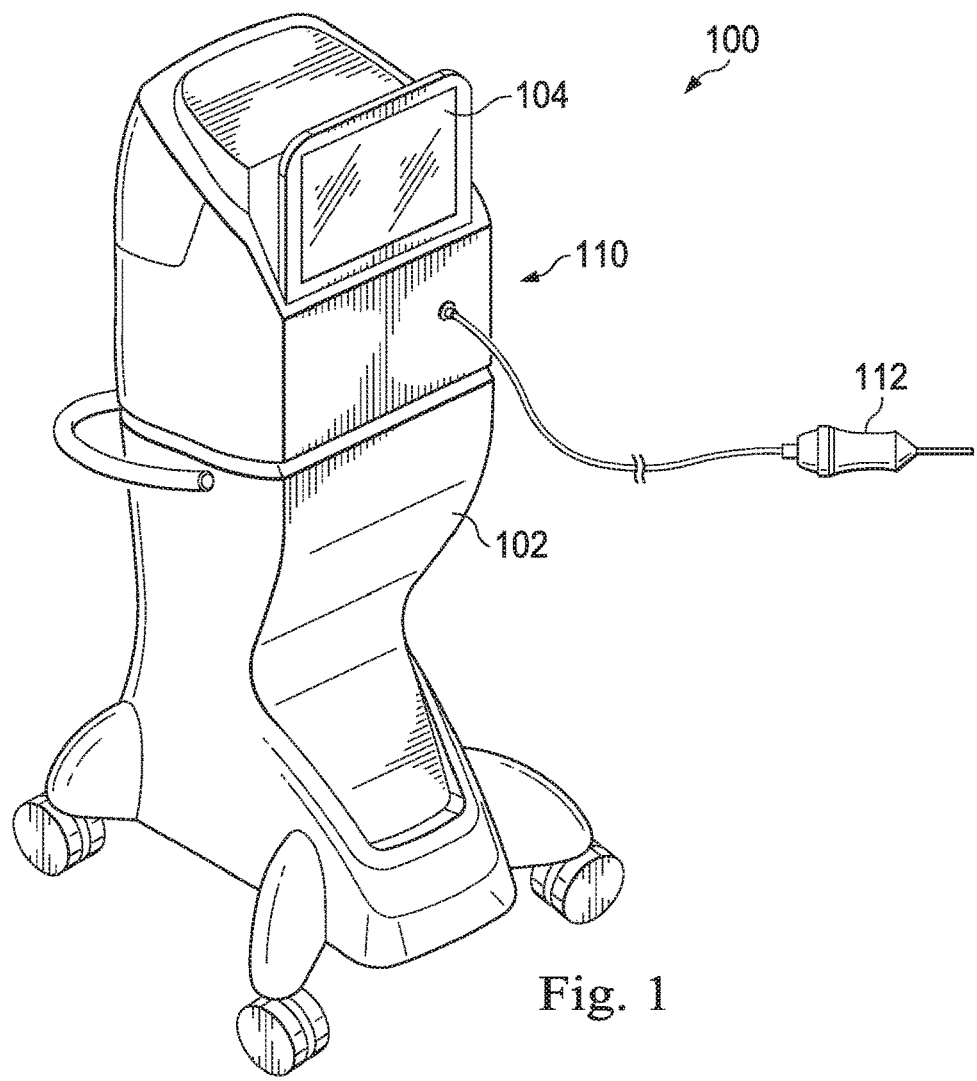
FIG. 1 is an illustration of an example ophthalmic surgical system.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure relates generally to devices, systems, and methods for cutting tissue within the eye using an end tissue cutter. In particular, the end tissue cutter may be provided at a distal end surface of a vitrectomy probe. The end tissue cutter allows for direct engagement with the target tissue, without additional maneuvering.

In particular, the cutter may include an outer cutting tube with an outer port formed at a distal end wall of the outer cutting tube. The outer port may receive tissue, and an inner cutting member may be disposed within the outer cutting tube to cut tissue received in the outer port. Because the outer port is provided at a distal end wall/surface of the vitrectomy probe, the vitrectomy probe may engage a target tissue directly. This allows a user/surgeon to point the vitrectomy probe directly at the target tissue to shave/remove the target tissue layer by layer. This may provide ease of use for the user/surgeon and improve surgical precision. For example, the end tissue cutter may have the ability to dissect tissues/membranes right at a surface near the retina without the use of additional instruments.

In some embodiments, the inner cutting member may include two or more cutting blades and the outer cutting tube may include two or more outer ports at the distal end. Different combinations of cutting blades and outer ports may allow for two or more cutting operations to be performed simultaneously.

FIG. 1 illustrates a vitrectomy surgical system, generally designated 100, according to an exemplary implementation. The vitrectomy surgical system 100 includes a base housing 102 and an associated display screen 104 showing data relating to system operation and performance during a vitrectomy surgical procedure. In some implementations, the base housing 102 may be mobile, for example, including wheels to facilitate movement as necessary. In an alternative implementation, the base housing 102 may not include wheels. The vitrectomy surgical system 100 includes a vitrectomy probe system 110 that includes a handheld vitrectomy probe 112, as will be discussed in more detail below with respect to subsequent figures.

Figure 2:
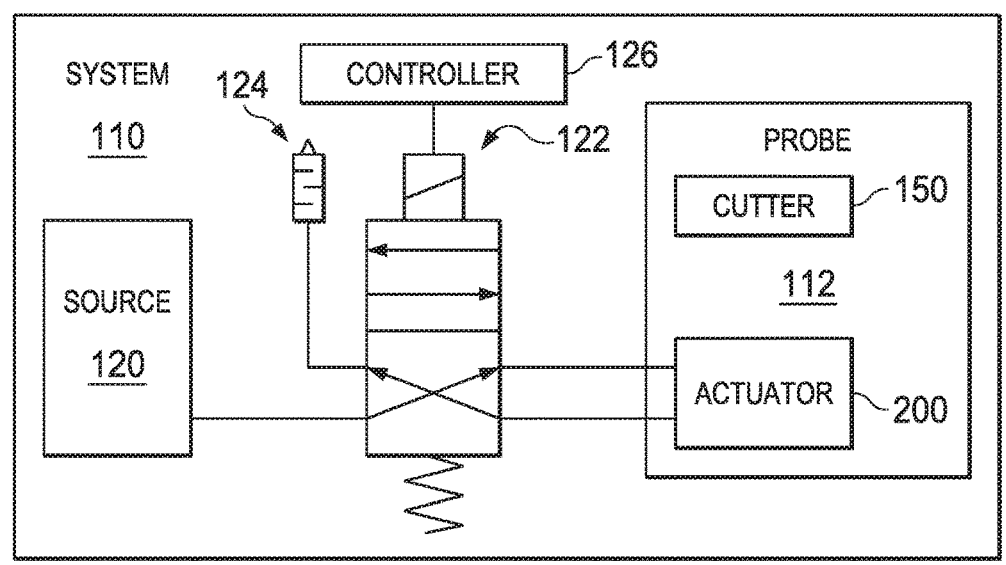
FIG. 2 is a block diagram of an example ophthalmic surgical system.

FIG. 2 is a schematic of exemplary components of the vitrectomy probe system 110. The vitrectomy probe system 110 includes the vitrectomy probe 112, a pneumatic pressure source 120, a probe driver shown as an adjustable directional on-off pneumatic driver 122 such as a valve, a muffler 124, and a controller 126. The controller 126 may be a processor that includes one or more processing cores capable of performing parallel or sequential operations. Alternatively, the controller 126 may be a dedicated piece of hardware such as an application specific integrated circuit (ASIC), to name just a few examples. The pneumatic pressure source 120, the driver 122, the muffler 124, and the vitrectomy probe 112 are in fluid communication with each other along lines representing flow paths or flow lines. The controller 126 is in electrical communication with the driver 122. In some implementations, the controller 126 controls operation of both the driver 122 and various aspects of the vitrectomy probe 112, including the frequency of oscillation by way of the actuator as well as a flow rate of fluid to and from the surgical site.

Figure 3:
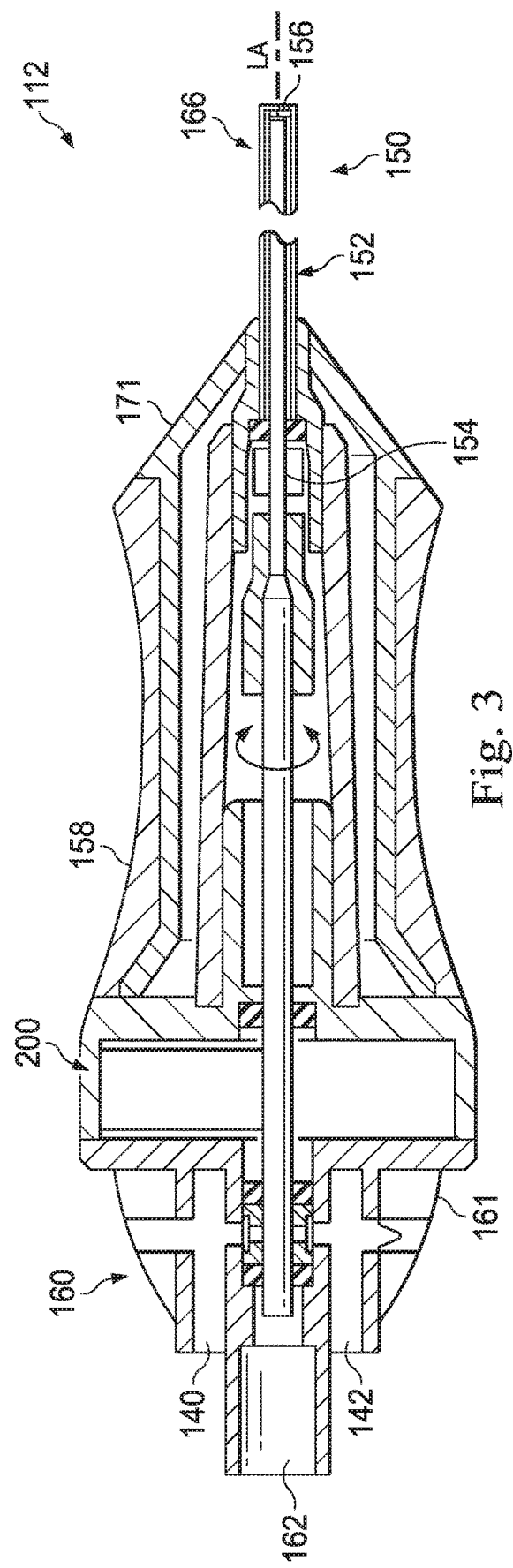
FIG. 3 is an illustration of an example vitrectomy probe.

FIG. 3 shows a partial cross-sectional illustration of an exemplary vitrectomy probe, for example, the vitrectomy probe 112 introduced in FIGS. 1 and 2. The vitrectomy probe 112 includes a housing 158 that is sized and shaped for grasping by a hand of a user. The vitrectomy probe 112 includes as its basic components a cutter 150 configured for insertion into the eye of a patient. The cutter 150 extends from a distal portion 171 of the housing 158 along a longitudinal axis LA. The cutter 150 includes an outer cutting tube 152 coupled to and extending from the housing 158. A port 156 that is sized and shaped to receive tissue within the eye is formed at a most-distal end surface of the outer cutting tube 152. The cutter 150 also includes an inner cutting member 154 shown in a non-sectional side view. The inner cutting member 154 may be rotatably disposed within the outer cutting tube 152. In that regard, the inner cutting member 154 is configured to rotate about its longitudinal axis, which in this implementation, is coaxial with the longitudinal axis LA. The inner cutting member 154 may be driven by an actuator 200 positioned within the housing 158. For example, the vitrectomy probe 112 may be a pneumatically driven probe that operates by receiving pneumatic pressure alternating through first and second ports 140 and 142. In some embodiments, the inner cutting member 154 may be driven by a motor to rotate continuously in one direction. The housing 158 includes an end piece 160 at a probe proximal end 161 with the first and second ports 140, 142 and one suction port 162 to provide aspiration of materials from the cutter 150.

Figure 4A:
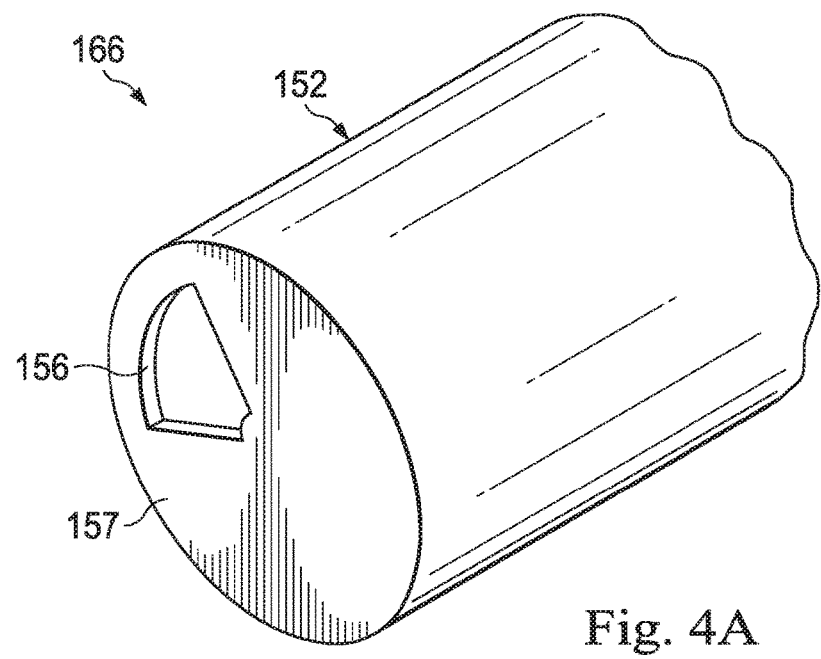
FIG. 4A is an illustration of a perspective view of an example distal portion of a vitrectomy probe.
Figure 4B:
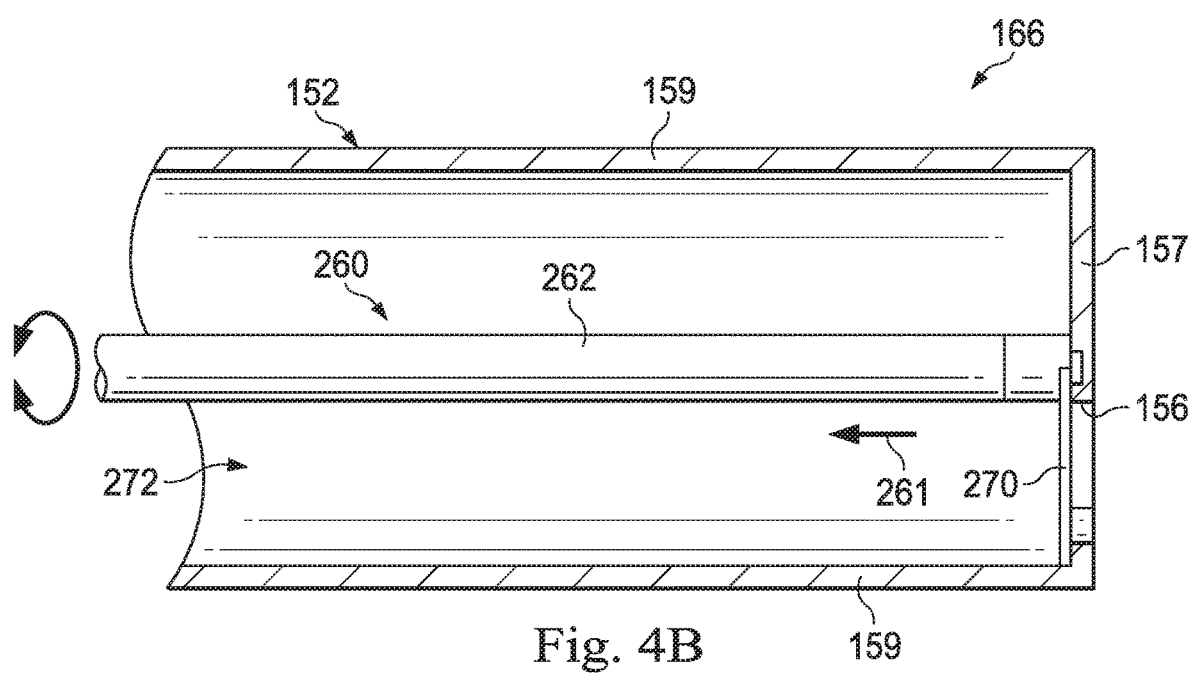
FIG. 4B is an illustration of a partial cross-sectional view of an example distal portion of a vitrectomy probe.

FIG. 4A is an illustration of a perspective view of the distal portion 166 of the cutter 150. As shown in FIG. 4A, the port 156 is formed at a distal end wall 157 of the outer tube 152. FIG. 4B is an illustration of a partial cross-sectional view of the distal portion 166 of the vitrectomy probe 112. The outer tube 152 may be formed by a cylindrical side wall 159 and the distal end wall 157. The outer port 156 is formed within the distal end wall 157 of the outer tube 152 and is sized to receive tissue based on application of suction at the port 162 (FIG. 2). The outer port 156 may be an aperture extending through the distal end wall 157.

In some embodiments, such as those illustrated in FIG. 4B, the inner cutting member 260 includes a rod 262 and one or more blades 270. In that regard, the inner cutting rod 262 may have a solid cross-section and may serve as a rotation axle. The outer cutting tube 152 may define a lumen 272, and the inner cutting member 260 may be disposed within the lumen 272. The inner cutting member 260 may have an outer diameter relatively smaller than an inner diameter of the outer cutting tube 152. Tissue cut by the inner cutting member 260 may be aspirated away from the eye through the aspiration lumen 272 adjacent the side of the inner cutting member 260, in the direction indicated by the arrow 261. The lumen 272 may be in fluid communication with the suction port 162 (FIG. 2) to aspirate fluid and/or cut tissue.

Figure 4C:
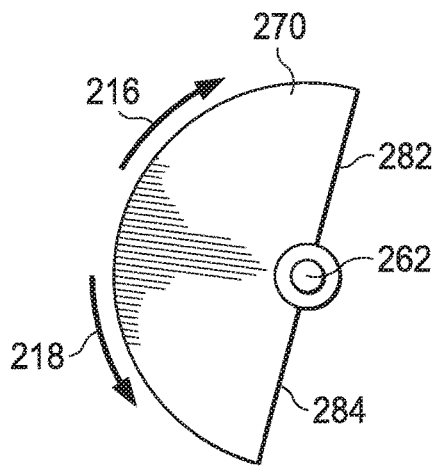
FIG. 4C is an illustration of an end view of an example cutting member.

One or more blades 270 may be disposed at a distal end of the inner cutting member 260. As shown in FIG. 4C, some implementations of a blade 270 may have a half-moon shape and may have one or more cutting edges 282 and 284. When the blade 270 has two cutting edges 282, 284, the inner cutting member 260 can cut tissue in the outer port 156 during rotation in both directions 216, 218. That is, the blade 270 may oscillate back and forth. The blade 270 may be configured to pass across the opening forming the outer port 156 to cut tissue within the outer port 156. The diameter of the blade 270 may be based on the diameters of the outer cutting tube 152 and/or the inner cutting member 260. Any of a variety of numbers and/or shapes of blades 170 may be disposed at the distal end of the inner cutting member 260 as suitable for different applications.

Figure 4E:
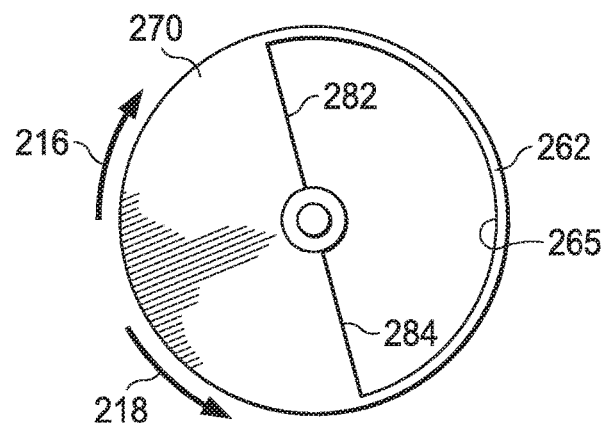
FIG. 4E is an illustration of an end view of another example cutting member.
Figure 4D:
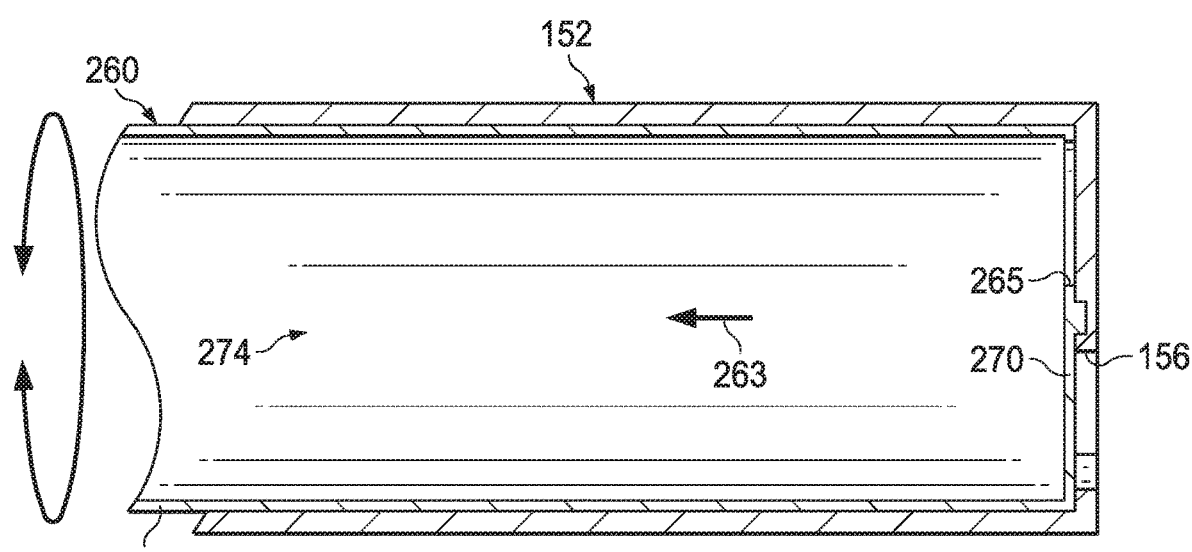
FIG. 4D is an illustration of a partial cross-sectional view of another example distal portion of a vitrectomy probe.

In other instances, such as those illustrated in FIG. 4D, the inner cutting member 260 is a tube, and defines a lumen 274. Tissue cut by the inner cutting member 260 may be aspirated away from the eye through the aspiration lumen 274 in the direction indicated by the arrow 263. The lumen 274 may be in fluid communication with the suction port 162 (FIG. 2) when a distal end opening 265 of the cutting member 260 aligns with the suction port 162 (FIG. 2). In this embodiment, one or more blades may be provided at the distal end surface of the tubular inner cutting member 260. As shown in FIG. 4E, the distal end opening 265 may be formed at a distal end wall/surface of the inner cutting member 260. The distal end opening 265 may define a blade 270 with one or more cutting edges 282, 284. The blade 270 may cooperate with the outer port 156 to cut tissue within the outer port 156 when the inner cutting member 260 rotates relative to the outer cutting tube 152.

The inner cutting member 260 may rotate back and forth alternating (reciprocating) between directions 216 and 218 or may rotate in only a single direction. The range and/or speed of rotation may be determined or set based on the size and shape of blade(s) and the size and shape of outer port(s). The range and/or speed of rotation also may be selected based on the surgical application. For example, for a larger size outer port, the corresponding blade may have a greater rotation range to move from one edge of the outer port to the other edge of the outer port to complete a cutting operation. For a smaller size outer port, a smaller rotation range may suffice to move the corresponding blade from one edge to the other edge of the outer port. In another example, the speed of rotation or actuation (e.g., reciprocation speed) may be increased to allow for finer cutting operations or for faster cutting.

Figure 5A:
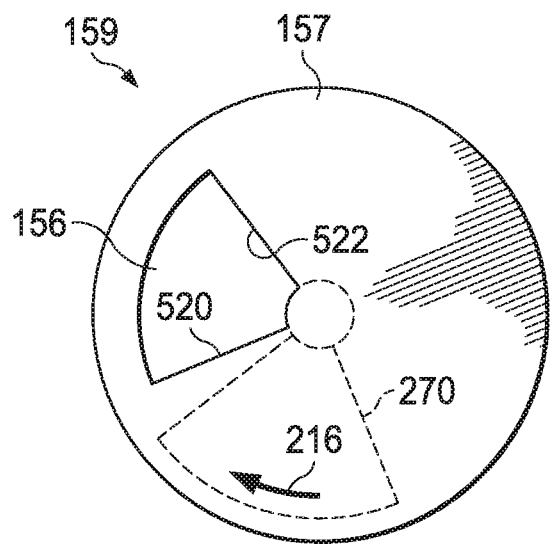
FIG. 5A is an illustration of an example distal portion of a vitrectomy probe during a first stage of a cutting operation.
Figure 5B:
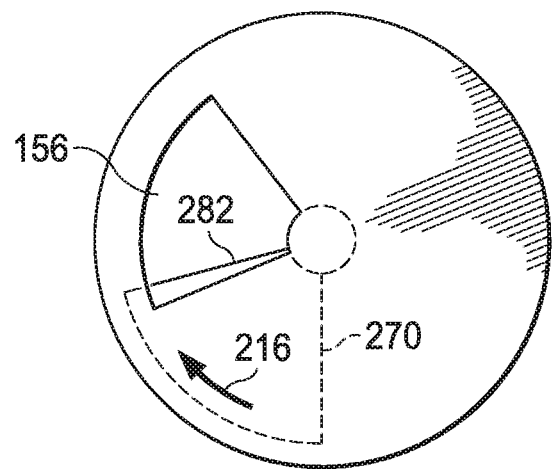
FIG. 5B is an illustration of an example distal portion of a vitrectomy probe during a second stage of a cutting operation.
Figure 5C:
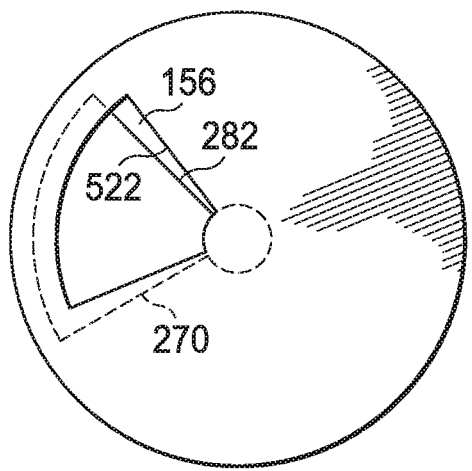
FIG. 5C is an illustration of an example distal portion of a vitrectomy probe during a third stage of a cutting operation.
Figure 5D:
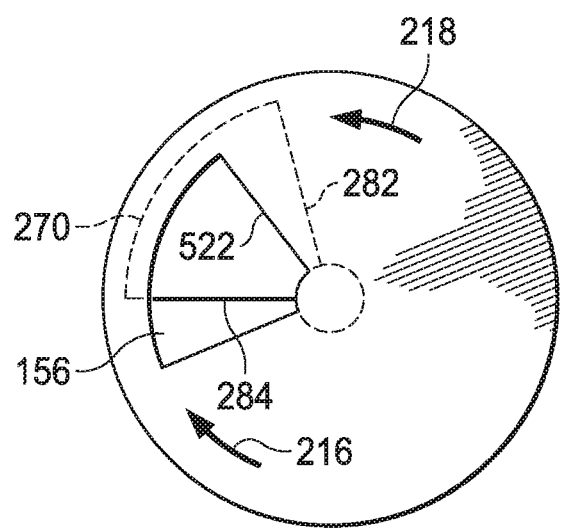
FIG. 5D is an illustration of an example distal portion of a vitrectomy probe during a fourth stage of a cutting operation.

FIGS. 5A-5D illustrate positions of an outer port 156 and a blade 270 at various stages of a cutting operation. As shown in FIG. 5A, the blade 270 may rotate underneath the end wall 157 in a direction 216 toward the outer port 156. In some embodiments, the blade 270 may slide/glide along an inner surface of the end wall 157. When the outer port 156 is not covered by the blade 270, a suction force of the aspiration system, such as a vacuum, may draw a tissue into the outer port 156. For example, the tissue is received in the outer port 156 as a result of suction at the suction port 162 (FIG. 3). As the cutting edge 282 of the blade 270 passes an edge 520 of the outer port 156 at an upstream side in the direction 216, the cutting edge 282 may begin to cut into the tissue that is protruding through the outer port 156 by the suction of the aspiration system. As shown in FIG. 5B, the blade 270 may continue to move in direction 216, such that the cutting edge 282 continues to cut into the tissue. As shown in FIG. 5C, the blade 270 may continue to move in direction 216 and the blade 270 may cover a larger portion of the outer port 156. As the cutting edge 282 of the blade 270 passes an edge 522 of the outer port 156 at a downstream side in the direction 216, the cutting edge 282 and the edge 522 may cooperate to shear off a portion or a layer of the tissue to complete one cutting operation. As shown in FIG. 5D, the blade 270 may continue to move in the direction 216. In some embodiments, the blade 270 may then move backward in the direction 218, such that the blade 270 returns to the initial position, as shown in FIG. 5A, ready for the next cutting operation. In such embodiments, the blade 170 may be actuated to reciprocate back and forth for each cutting operation. In other embodiments, the blade 270 may rotate in only a single cutting direction.

In some embodiments, the blade 270 may have two cutting edges 282 and 284 disposed at opposite sides of the blade 270 as shown. As such, in FIG. 5D, the blade 270 may continue to move in the direction 216 until the cutting edge 284 of the blade 270 passes the edge 522 of the outer port 156. After the cutting edge 284 of the blade 270 passes the edge 522 of the outer port 256, the outer port 156 may be completely open and may draw another portion of the tissue into the outer port 156 by the suction force of the aspiration system. The blade 270 may stop moving in the direction 216 and may begin to reverse and move in the direction 218. As the blade moves in the direction 218, the cutting edge 284 of the blade 270 may pass the edge 522 of the outer port and may begin to cut into the new portion of the tissue. The cutting edge 284 may continue to cut into the new portion of the tissue as the blade move in the direction 218. When the cutting edge 284 of the blade 270 passes the edge 520 of the outer port 156, the cutting edge 284 may cooperate with the edge 520 to shear off the new portion of the tissue to finish the second cutting operation. The blade 270 may return to the initial position, as shown in FIG. 5A, for the next actuation. Thus, the two cutting edges 282 and 284 of the blade 270 may allow for two cutting operations for each actuation of the blade 270 (e.g., one cutting operation rotating in the direction 216 and another cutting operation rotating in the direction 218).

In these types of implementations, the blade 270 and the inner cutting member 260 travel in the directions 216, 218 along an arc. The arc follows a path that includes less than the 360° rotation associated with a complete revolution of the blade 270. In that regard, depending upon the implementation, the arc of the blade 270 and the inner cutting member 260 may be less than 120°. In other implementations, the arc of the blade 270 and the inner cutting member 260 may be less than 90°. In yet other implementations the arc may be less than 45°. In yet others, the arc may be less than 30°. Other suitable arc values are also contemplated. Smaller arc values result in smaller travel distances. These in turn may enable higher reciprocation speeds, resulting in higher cutting rates.

In some embodiments, the inner cutting member 260 may rotate continuously in either direction 216 or direction 218. A rotary driving mechanism (e.g., a motor) may be utilized to provide a continuous rotational drive to the cutting member 260. The rotational speed of the cutting member 260 may be selected and/or adjusted as suitable for the surgical operation. For example, a faster rotational speed may correspond to a greater cutting rate to provide finer tissue cutting.

Figure 5E:
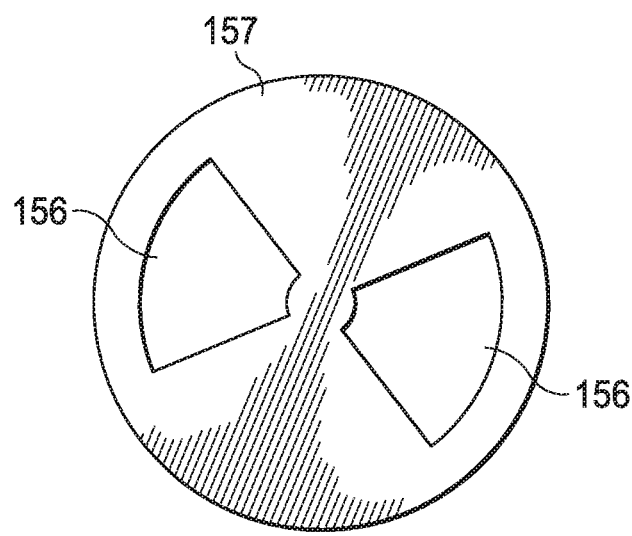
FIG. 5E is an illustration of an end view of an example distal portion of a vitrectomy probe with two ports.
Figure 5F:
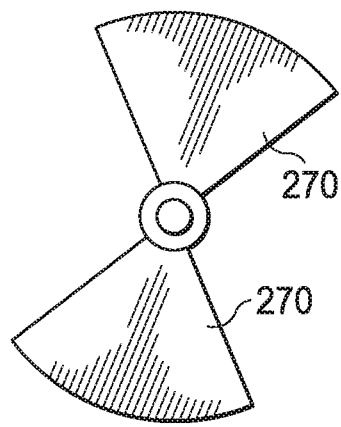
FIG. 5F is an illustration of an example cutting member with two cutting blades.

Although one outer port and one blade were shown in FIGS. 5A-5D, in other embodiments, multiple outer ports or multiple blades may be utilized based on the surgical application. For example, as shown in FIG. 5E, two outer ports 156 may be provided in the distal end wall 157 to allow two cutting sites/locations. Any number of outer ports 156 (e.g., one, two, three, four, and etc.) may be provided based on a surgical application. In another example, as shown in FIG. 5F, two blades 270 may be provided. Any number of blades 270 (e.g., one, two, three, four, and etc.) may be provided based on a surgical application.

Any of a variety of different sizes and shapes of the blade and/or outer port may be utilized based on the type of surgical application. As shown in FIGS. 5A-5D, the outer port 156 and the blade 270 may have a wedge shape. In another example, as shown in FIG. 4C, the blade may have a half-moon shape. Different numbers, sizes, and shapes of blades may be paired/combined with different numbers, sizes, and/or shapes of outer ports to form different combinations of end tissue cutters based on requirements in different types of surgical applications. For example, one outer port combined with two or more blades may allow for faster cutting rates at the same location. In another example, two outer ports combined with two or more blades may allow for two cutting operations to be performed simultaneously at two different locations. A larger size outer port may correspond to a larger actuation/rotation distance for the blade(s), but may allow for better aspiration flow. A smaller size outer port may allow for small actuation/rotation distance for the blade(s) and faster actuation rate for higher cutting speed.

Figure 5G:
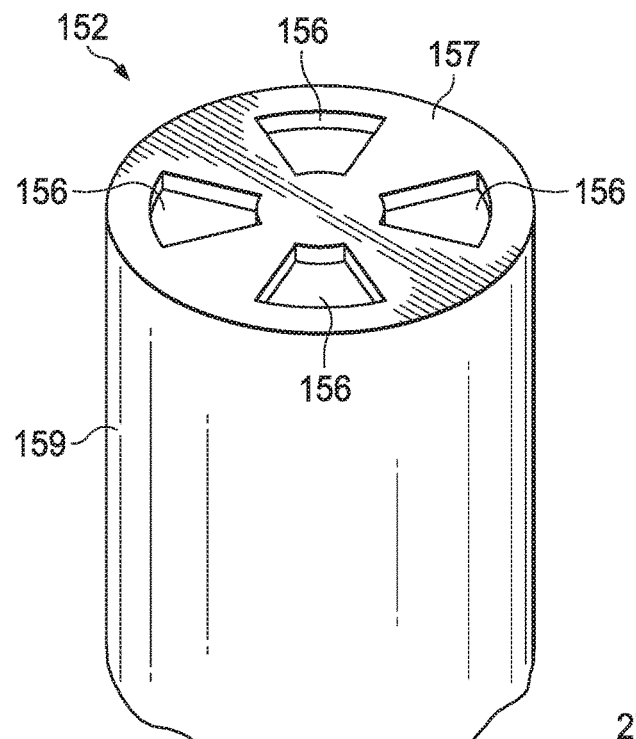
FIG. 5G is an illustration of an example distal portion of a vitrectomy probe with four ports.
Figure 5H:
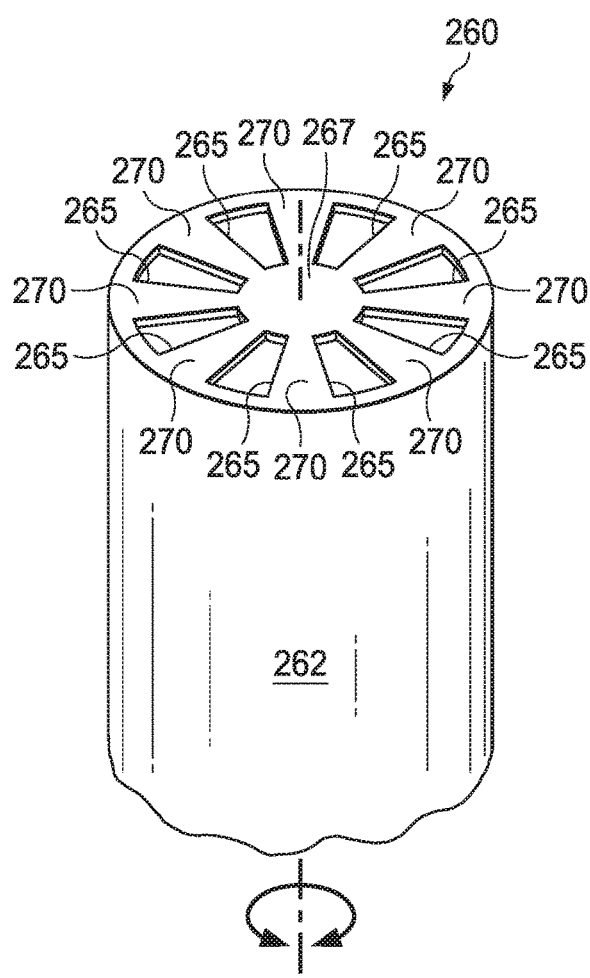
FIG. 5H is an illustration of an example cutting member with eight cutting blades.
Figure 5I:
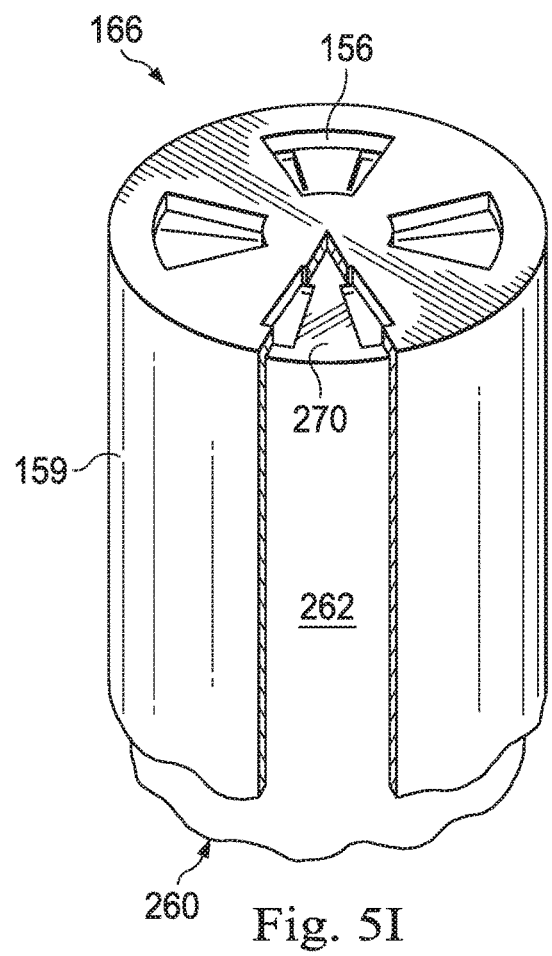
FIG. 5I is an illustration of an example distal portion of the vitrectomy probe of FIG. 5G combined with the cutting member of FIG. 5H.

As shown in FIG. 5G, four ports 156 may be provided in the distal end wall 157. The four ports 156 may be radially spaced and evenly spaced apart. As shown in FIG. 5H, the inner cutting member 260 may be provided with eight cutting blades 270. The inner cutting member 260 of FIG. 5G may be disposed in the outer cutting member of FIG. 5G. In particular, eight openings 265 are formed in the distal end wall 267 of the cutting member 260 to define the eight cutting blades 270. The plurality of cutting blades 270 may provide for an increase in cutting speed. Further, the eight openings 265 may allow for better aspiration flow during the cutting process. As shown in FIG. 5I, a width of the cutting blade 270 may be less than a width of the port 156. Thus, the cutting blade 270 may leave the port 156 open during the cutting process, which allows for the port duty cycle to approach 100%. This may increase vitreous mass flow rate through the ports 156 thereby improving aspiration.

Figure 5J:
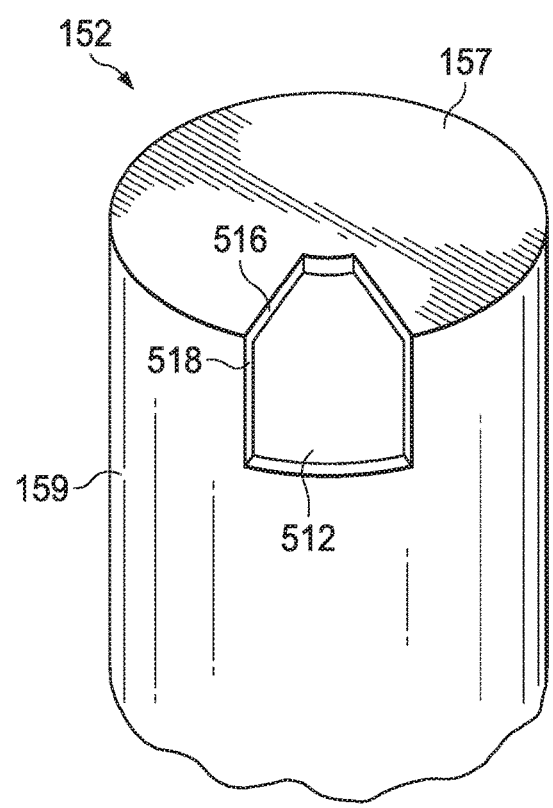
FIG. 5J is an illustration of an example distal portion of a vitrectomy probe with a two-dimensional port.
Figure 5K:
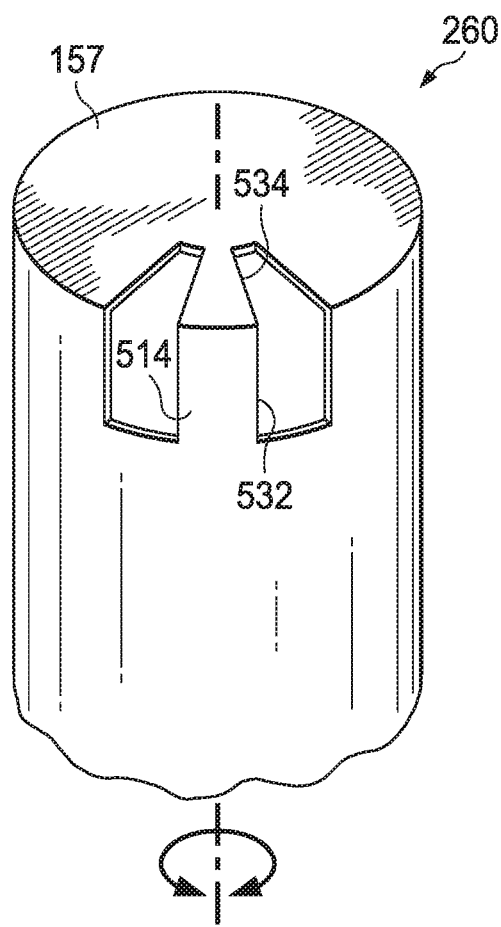
FIG. 5K is an illustration of an example cutting member with a two-dimensional blade.

In another example, as shown in FIG. 5J, a two-dimensional port 512 may be provided. The two-dimensional port 512 may be formed at a corner of the distal end wall 157 and the cylindrical side wall 159 of the outer cutting tube 152. In particular, the two-dimensional port 512 may be formed by cutouts from both the distal end wall 157 and the cylindrical side wall 159 of the outer cutting tube 152. The two-dimensional port 512 may draw tissue from two directions, such as from the front and from the side of the outer cutting tube 152.

Figure 5L:
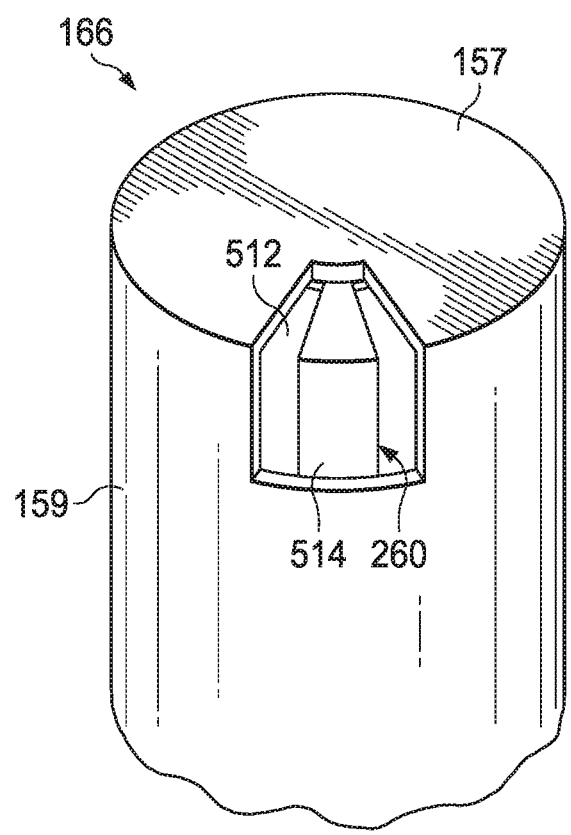
FIG. 5L is an illustration of an example distal portion of the vitrectomy probe of FIG. 5J combined with the two-dimensional cutting member of FIG. 5K.

The two-dimensional port 512 may be combined with a two-dimensional cutting blade 514, as shown in FIG. 5L. The two-dimensional cutting blade 514 may have two cutting edges 532 and 534, with the cutting edge 532 arranged along a cylindrical wall side of the cutting member 260 and the cutting edge 543 arranged along a distal end wall of the cutting member 260. As shown in FIG. 5L, The cutting edge 532 of the two-dimensional cutting blade 514 may coordinate with an edge 518 of the two-dimensional port 512 to cut or shear a tissue protruding into the two-dimensional cutting blade 514 from the cylindrical wall side of the outer cutting tube 152. The cutting edge 534 of the two-dimensional cutting blade 514 may coordinate with an edge 516 of the two-dimensional port 512 to cut or shear a tissue protruding into the two-dimensional cutting blade 514 from the distal end wall side of the outer cutting tube 152. Thus, the two-dimensional port/blade may allow cutting to occur both at the distal end and at the cylindrical side surface of the outer cutting tube 152 (e.g., corner cutting). For example, the two-dimensional port/blade may allow tissue cutting at different locations along a retinal surface depending on the surgical objective.

Figure 6:
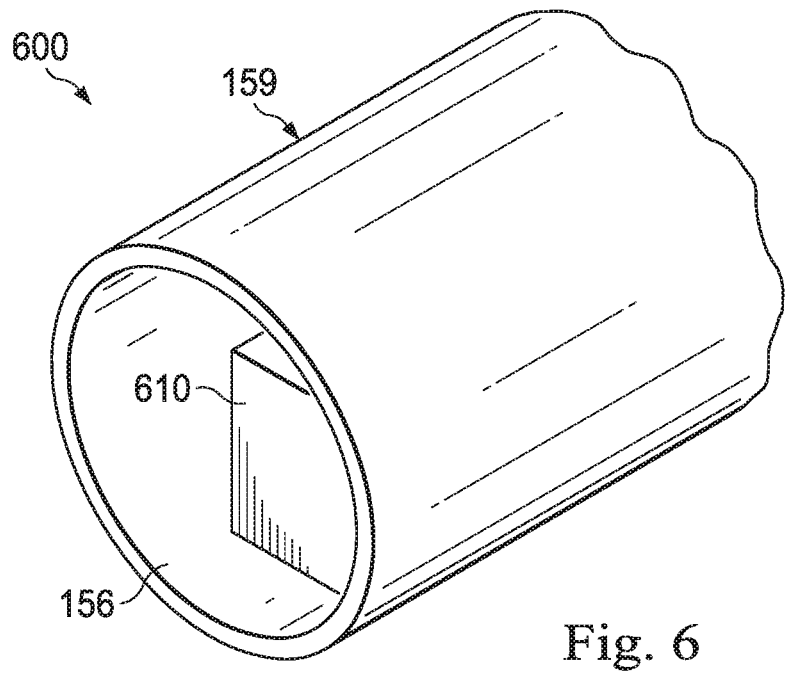
FIG. 6 is an illustration of a perspective view of an example distal portion of a vitrectomy probe including a laser cutting portion.

In some embodiments, as shown in FIG. 6, a laser based end cutter 600 may be provided. A laser emitter 610 may be encapsulated at a distal end of the outer cutting tube 157. The outer port 156 may serve as an aspiration port for drawing a tissue into the outer port 156. The laser emitter 610 may be configured to emit laser to ablate the tissue drawn in to the outer port 156. The laser emitter 610 may include optical components, such as a prism and/or a mirror configured to direct or bend a laser ray toward the tissue at the outer port 156. For example, an optical wave guide may be provided and configured to scan the laser ray across the outer port 156 to ablate the tissue.

Figure 7:
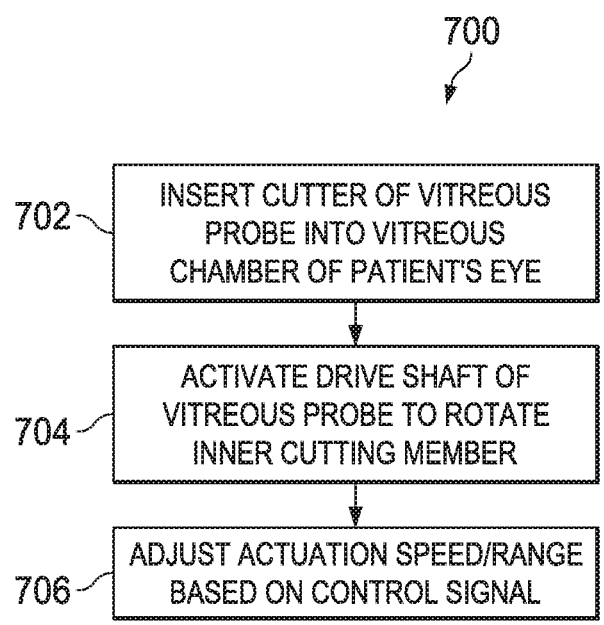
FIG. 7 is a flow diagram of an ophthalmic surgical method.

FIG. 7 is a flow diagram of an ophthalmic surgical method 700. It is understood that the elements of method 700 may be performed in a different order, and additional elements can be provided before, during, and after these elements, and/or some of the elements described can be replaced or eliminated in other implementations. One or more of the elements of the method 700 can be carried out by a medical professional, such as a surgeon, during an ophthalmic surgical procedure.

At 702, the method 700 includes inserting a cutter of a vitreous probe into a vitreous chamber of the patient's eye. For example, a surgeon may insert at least the distal portion 166 of the cutter 150 (FIG. 3) into the patient's eye. In that regard, the cutter 150 can include the outer cutting tube 152. A distal end wall of the outer cutting tube 152 includes an outer port or aperture 156 that is sized and shaped to receive tissue. The cutter 150 can also include the rotatable inner cutting member 154 positioned within the outer cutting tube 152.

During a vitrectomy procedure, the surgeon typically inserts the cutter 150 of the vitrectomy probe 112 into the posterior segment and/or or vitreous chamber of the eye via an incision through the sclera in the pars plana. Such an incision is called a sclerotomy. The surgeon typically also inserts a light source and the infusion cannula into the eye via similar incisions. While viewing the posterior segment and/or vitreous chamber under a microscope and with the aid of the light source, the surgeon cuts and aspirates away vitreous using the vitrectomy probe 112 to gain access to the area of interest (e.g., the site of a retinal detachment or tear). The surgeon may also use the vitrectomy probe 112 to remove any membrane that has contributed to the retinal detachment. During this portion of the surgery, a saline solution is typically infused into the eye via the infusion cannula to maintain the appropriate intraocular pressure.

At 704, the method 700 may include activating a drive shaft of the vitreous probe 112 to rotate the inner cutting member 260 to cut tissue in the outer port 156 of the vitreous probe. For example, a rotating shaft may be mechanically coupled to the inner cutting member 154 such that rotation of the rotating shaft causes corresponding rotation of the inner cutting member. The distal portion of the inner cutting member may include one or more cutting blades 270. Rotation of the inner cutting member causes one or more of the cutting blades 270 to travel across the outer port(s) of the outer cutting tube and cut the tissue.

At 706, the controller 126 may set/adjust the actuation speed and actuation range of the cutter based on a control signal, such as based on the type of end tissue cutter and/or based on user input. For example, a surgeon may control the speed of the cutter by a foot pedal. In another example, the controller 126 may automatically set/adjust the actuation speed based on the type of vitrectomy probe attached to the system. The vitrectomy probe may include a tag, such as an RFID tag, that may identify the model/type of the vitrectomy probe. Different types of end tissue cutters may have different combinations of outer port(s) and blade(s) arrangements which may correspond to different actuation speed and range. For example, an end tissue cutter with larger outer ports may correspond to a larger actuation range.

When the vitrectomy probe is attached to the vitrectomy surgical system 100, the controller 126 may detect the tag attached to the vitrectomy probe and may determine the type of vitrectomy probe attached to the vitrectomy surgical system 100 based on the tag. For example, the controller 126 may use a look-up table to determine actuation parameters for the attached vitrectomy probe. For instance, an end tissue cutter with two outer ports and two cutting blades may have a set of actuation parameters different from those of an end tissue cutter with one outer port and one blade. The actuation parameters may allow the controller 126 to set proper actuation speed and actuation range (e.g., maximum speed and maximum travel range) for the particular end tissue cutter. During operation, the controller 126 may control/limit the actuation speed/range based on the actuation parameters. Further, the controller 126 may receive user input and may adjust the actuation speed/range based on the user input.

Implementing the systems, methods and devices disclosed herein may provide advantages not obtained by conventional vitrectomy probes. The advantages described herein may provide an end tissue cutter with a cutting interface disposed in a distal end wall of an outer cutting tube of a vitrectomy probe. This allows for direct engagement between the cutting interface and a target tissue and easy maneuvering for users/surgeons. For example, a surgeon may simply point the tip of the vitrectomy probe directly at the target tissue to begin the cutting operation (e.g., point and cut). Further, with the reduced PTTD, the vitrectomy probe may improve the surgical precision. Furthermore, using a rotational blade with two cutting edges that permit tissue to be cut during rotation in two opposite directions may improve the cutting capacity of the probe.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitrectomy probe comprising:
   a housing;
   a cutter extending from the housing and configured to penetrate and treat an eye of a patient, the cutter comprising:
      an outer cutting tube coupled to the housing, the outer cutting tube having an outer port formed only in a flat distal end wall of the outer cutting tube and configured to receive tissue, wherein the port does not extend along the sides of the outer cutting tube; and
      an inner cutting member disposed within the outer cutting tube to cut tissue received in the outer port;

wherein the inner cutting member comprises a cutting blade configured to move across the outer port and coordinate with the outer port to cut tissue received in the outer port;

wherein the inner cutting member is configured to be rotated continuously or in a reciprocating fashion along a longitudinal axis of the outer cutting tube;

wherein the flat distal end wall of the outer cutting tube is in a plane perpendicular to the longitudinal axis of the outer cutting tube;

wherein the outer port is one of a plurality of outer ports in the outer cutting tube at the flat distal end and wherein the plurality of ports are in the plane perpendicular to the longitudinal axis of the outer cutting tube.

2. The vitrectomy probe of claim 1, wherein the inner cutting member comprises a rod extending in the outer cutting tube along the longitudinal axis of the outer cutting tube and the cutting blade is disposed at a distal end of the rod.

3. The vitrectomy probe of claim 2, wherein the outer cutting tube comprises a lumen sized to pass tissue adjacent the rod for aspiration from the eye.

4. The vitrectomy probe of claim 2, wherein the cutting blade comprises a cutting edge and the rod is driven by a motor to rotate the cutting blade continuously in a particular direction with the cutting edge being a leading edge.

5. The vitrectomy probe of claim 2, wherein the rod is driven by an actuator to rotate the cutting blade in two opposite directions to reciprocate the cutting blade back and forth over the outer port.

6. The vitrectomy probe of claim 5, wherein the cutting blade comprises two cutting edges disposed at opposite sides of the cutting blade and one of the two cutting edges is configured to cut tissue in the outer port when the cutting blade is rotated in a first direction and the other one of the two cutting edges is configured to cut tissue in the outer port when the cutting blade is rotated in a second direction opposite the first direction.

7. The vitrectomy probe of claim 2, wherein the rod comprises an aspiration lumen configured to aspirate tissue from the eye.

8. The vitrectomy probe of claim 1, wherein the inner cutting member comprises a laser cutting device configured to ablate tissue received in the outer port.

9. The vitrectomy probe of claim 1, wherein the inner cutting member comprises two or more cutting blades, and wherein the two or more cutting blades and the plurality of outer ports are configured to coordinate with each other to perform two or more cutting operations simultaneously.

10. The vitrectomy probe of claim 1, wherein the plurality of outer ports are radially and evenly spaced apart.

11. An ophthalmic surgical system, the system comprising:
a vitrectomy probe comprising:
a housing;
a cutter extending from the housing and configured to penetrate and treat an eye of a patient, the cutter comprising:
an outer cutting tube coupled to the housing, the outer cutting tube having an outer port formed only in a flat distal end wall of the outer cutting tube and configured to receive tissue, wherein the port does not extend along the sides of the outer cutting tube; and
an inner cutting member disposed within the outer cutting tube to cut tissue received in the outer port;
wherein the inner cutting member comprises a cutting blade configured to move across the outer port and coordinate with the outer port to cut tissue received in the outer port; and
an actuator configured to impart rotational motion to the inner cutting member; and
a controller configured to drive the actuator to rotate the inner cutting member continuously or in a reciprocating fashion along a longitudinal axis of the outer cutting tube;
wherein the flat distal end wall of the outer cutting tube is in a plane perpendicular to the longitudinal axis of the outer cutting tube;
wherein the outer port is one of a plurality of outer ports in the outer cutting tube at the flat distal end and wherein the plurality of ports are in the plane perpendicular to the longitudinal axis of the outer cutting tube.

12. The system of claim 11, wherein the controller is configured to adjust a rotational speed of the inner cutting member to adjust a cutting rate.

13. The system of claim 11, wherein the controller is configured to adjust a reciprocation speed of the inner cutting member to adjust a cutting rate.

14. The system of claim 11, wherein the controller is configured to adjust a rotation range of the inner cutting member based on a type of the outer port of the outer cutting tube.

15. The system of claim 11, wherein the vitrectomy probe comprises an Radio Frequency Identification (RFID) tag indicating a type of vitrectomy probe and the controller is configured to detect the type of vitrectomy probe based on the RFID tag and set an actuation speed and an actuation range of the inner cutting member based on the type of vitrectomy probe.

16. The ophthalmic surgical system of claim 11, wherein the plurality of outer ports are radially and evenly spaced apart.

17. An ophthalmic surgical method comprising:
inserting a cutter of a vitreous probe into a vitreous chamber of an eye of a patient, the cutter comprising:
an outer cutting tube having an outer port formed only in a flat distal end wall of the outer cutting tube and configured to receive tissue through the outer port, wherein the port does not extend along the sides of the outer cutting tube, and
a rotatable inner cutting member positioned within the outer cutting tube and rotatable past the outer port, wherein the inner cutting member comprises a cutting blade configured to move across the outer port and coordinate with the outer port to cut tissue received in the outer port; and
rotating the inner cutting member continuously or in a reciprocating fashion along a longitudinal axis of the outer cutting tube to cut tissue in the outer port;
wherein the flat distal end wall of the outer cutting tube is in a plane perpendicular to the longitudinal axis of the outer cutting tube;
wherein the outer port is one of a plurality of outer ports in the outer cutting tube at the flat distal end and wherein the plurality of ports are in the plane perpendicular to the longitudinal axis of the outer cutting tube.

18. The method of claim 17, further comprising adjusting one or more of an actuation speed and an actuation range of the inner cutting member based on a control signal.

* * * * *